United States Patent [19]

Grollier

[11] Patent Number: 5,549,886
[45] Date of Patent: Aug. 27, 1996

[54] PHOTOSTABLE FILTERING COSMETIC COMPOSITION

[75] Inventor: Jean F. Grollier, Paris, France

[73] Assignee: L'Oreal, Paris, France

[21] Appl. No.: 332,065

[22] Filed: Nov. 1, 1994

Related U.S. Application Data

[62] Division of Ser. No. 854,883, Mar. 20, 1992, Pat. No. 5,393,515, which is a continuation of Ser. No. 399,836, Aug. 24, 1989, abandoned.

Foreign Application Priority Data

Aug. 24, 1988 [FR] France .................. 88 11178

[51] Int. Cl.$^6$ .................................................. A61K 7/42
[52] U.S. Cl. ..................................... 424/59; 514/938
[58] Field of Search ........................ 424/59; 514/938

[56] References Cited

U.S. PATENT DOCUMENTS

| | | | |
|---|---|---|---|
| 4,804,531 | 2/1989 | Grollier | 424/59 |
| 4,837,010 | 6/1989 | Hotta et al. | 424/59 |
| 5,384,115 | 1/1995 | Bissett et al. | 514/938 |
| 5,393,515 | 2/1995 | Grollier | 424/47 |

FOREIGN PATENT DOCUMENTS

| | | | |
|---|---|---|---|
| 2121801 | 1/1984 | United Kingdom | 424/59 |
| 2123418 | 2/1984 | United Kingdom | 424/59 |
| 2133985 | 8/1984 | United Kingdom | 424/59 |
| 2170105 | 7/1986 | United Kingdom | 424/59 |
| 2198944 | 6/1988 | United Kingdom | 424/59 |
| 2200552 | 8/1988 | United Kingdom | 424/59 |

*Primary Examiner*—Shelley A. Dodson
*Attorney, Agent, or Firm*—Cushman Darby & Cushman, L.L.P.

[57] ABSTRACT

The invention relates to a photostable filtering emulsion containing in association, in the aqueous phase, a photostable filter with a wide absorption band constituted by partially or totally neutralized benzene-1,4-[di(3-methylidene-10-camphosulphonic)] acid, and in the oily phase a photostable system which filters the UV-A rays containing at least one of the following compounds: N-(2-ethylhexyl)-3-[(3'-methoxy-4'-n-butoxy)benzylidene]-10-camphosulphonamide (compound 2), 4-(1,1-dimethylethyl)-4'-methoxydibenzoylmethane (compound 3) and 4-isopropyldibenzoylmethane (compound 4), these two latter compounds 3 and 4 being photochemically stabilized by at least one fat-soluble filter of $\lambda_{max}$ less than 330 nm chosen from the following benzylidene camphor derivatives: benzylidene camphor (compound 5), p-methylbenzylidene camphor (compound 6), N-(2-ethylhexyl)-4-(3'-methylidene camphor)benzene sulphonamide (compound 7) and 3-methoxy-4-n-butoxybenzylidene camphor (compound 8).

This composition is intended to protect the skin from UV rays of wavelengths between 280 and 380 nm.

3 Claims, No Drawings

PHOTOSTABLE FILTERING COSMETIC COMPOSITION

This is a division of application Ser. No. 07/854,883, filed Mar. 20, 1992, now U.S. Pat. No. 5,393,575 which is a Continuation of application Ser. No. 07/399,836, filed Aug. 24, 1989, abandoned.

The present invention relates to a photostable filtering cosmetic composition in the form of an emulsion, intended to protect the skin from UV radiation, containing, in association, a photostable filter with a wide absorption band, of a particular type, in the aqueous phase, and at least one photostable UV-A filter in the oily phase. The present invention also relates to the use of such a composition for the protection of the skin against UV rays.

It is known that light radiation of wavelengths between 280 nm and 400 nm allows browning of the human epidermis, and that the rays of wavelengths between 280 and 320 nm, known under the name of UV-B, cause erythemas and cutaneous burns which can harm the development of bronzing; this UV-B radiation must therefore be filtered out.

It is also known that the UV-A rays, of wavelengths between 320 and 400 nm, which cause browning of the skin, are capable of inducing alteration of the latter, in particular in the case of sensitive skin or of skin continuously exposed to solar radiation. The UV-A rays cause, in particular, a loss of elasticity of the skin and the appearance of wrinkles, leading to premature ageing. They favour the triggering of the erythematous reaction or amplify this reaction in certain subjects, and can even be the origin of phototoxic or photoallergic reactions. It is therefore completely desirable to filter the UV-A radiation.

As, in addition, the solar UV-A radiation is quantitively greater than the solar UV-B radiation, it can be seen that there is an interest in using compositions which absorb strongly in the UV-A zone, and therefore are enriched in compounds absorbing in that region.

French Patent No. 2,528,420 describes compounds which strongly absorb UV rays over a wide band, and in particular the derivatives of benzene[di(3-methylidene-camphor)] which are sulphonated in position 10 of the camphor, of which benzene-1,4-[di(3-methylidene-10-camphosulphonic)] acid, which will hereinafter be called compound 1. This photostable compound has an absorption maximum in the UV-A at 342 nm, and its absorption in the UV-B region, corresponding to the erythematous rays, is substantial. It therefore constitutes a wide band filter.

Its sulphonic groups confer on it the characteristic of solubility in water. Unfortunately, for cosmetic reasons, it is desirable not to use this compound at very great concentrations.

In addition, this compound does not have very good resistance to sea and swimming-pool water or to sweat, which could require repeated applications during exposure to the sun.

The applicant has discovered that by associating this wide band photostable filter, dissolved in the aqueous phase, with a photostable filtering system containing at least one UV-A filter dissolved in the oily phase of an emulsion, a very good protection against solar radiation is obtained with, in addition, improved water resistance.

The photostable UV-A filtering system dissolved in the oily phase comprises at least one of the following UV-A filters:

N-(2-ethylhexyl)-3-[(3'-methoxy-4'-n-butoxy)benzylidene]-10-camphosulphonamide, described in French Patent No. 2,529,887 (compound 2)

4-(1,1-dimethylethyl)-4'-methoxydibenzoylmethane, sold under the name "Parsol 1789" by the Givaudan company (compound 3), 4-isopropyldibenzoylmethane, sold under the name "Eusolex 8020" by the Merck company (compound 4), the two compounds 3 and 4 being photochemically stabilized by association with one or more of the following fat-soluble filters of $\lambda_{max}$ less than 330 nm:

compound 5: benzylidene camphor, compound 6: p-methylbenzylidene camphor, sold under the name "Eusolex 6300" by the Merck company, compound 7: N-(2-ethylhexyl)-4-(3'-methylidene camphor)benzene sulphonamide, described in French Patent No. 2,529,887, compound 8: 3-methoxy-4-n-butoxybenzylidene camphor, described in French Patent No. 2,430,938.

The subject of the present invention is therefore a photostable filtering cosmetic composition in the form of an emulsion, intended to protect the skin from UV radiation of wavelengths between 280 and 380 nm, containing in association in the aqueous phase, a wide absorption band photostable filter constituted by partially or totally neutralized benzene-1,4-[di(3-methylidene-10-camphosulphonic)] acid, and in the oily phase a photostable system which filters the UV-A rays comprising at least one of the following compounds: N-(2-ethylhexyl)-3-[(3'-methoxy-4'-n-butoxy)benzylidene]-10-camphosulphonamide (compound 2), 4-(1,1-dimethylethyl)-4'-methoxydibenzoylmethane (compound 3) and 4-isopropyldibenzoylmethane (compound 4), the two latter compounds 3 and 4 being photochemically stabilized by one or more fat-soluble filters of $\lambda_{max}$ less than 330 nm chosen from benzylidene camphor (compound 5), p-methylbenzylidene camphor (compound 6), N-(2-ethylhexyl)-4-(3'-methylidene camphor)benzene sulphonamide (compound 7) and 3-methoxy-4-n-butoxybenzylidene camphor (compound 8).

One method of implementation of the invention consists in using in the oily phase N-(2-ethylhexyl)-3-[(3'-methoxy-4'-n-butoxy)benzylidene]-10-camphosulphonamide (compound 2) or 4-(1,1-dimethylethyl)-4'-methoxydibenzoylmethane (compound 3), photochemically stabilized by benzylidene camphor (compound 5), N-(2-ethylhexyl)-4-(3'-methylidene camphor)benzene sulphonamide (compound 7) or 3-methoxy-4-n-butoxybenzylidene camphor (compound 8), taken alone or in combination, or even an association of compounds 2 and 3 with one or more of compounds 5, 7 and 8.

The particularly preferred photostable emulsion contains, in the oily phase, 4-(1,1-dimethylethyl)-4'-methoxydibenzoylmethane (compound 3) photochemically stabilized with p-methylbenzylidene camphor (compound 6).

A subject of the present invention is also a process for the protection of the human epidermis against UV rays of wavelengths between 280 and 380 nm, consisting in applying on the skin an effective quantity of the abovementioned photostable filtering cosmetic composition in the form of an emulsion.

To neutralize the benzene-1,4-[di(3-methylidene-10-camphosulphonic)] acid, alkali hydroxides, and more particularly sodium or potassium hydroxides, ammonia and the alkanolamines can be used, triethanolamine being preferred.

In the filtering cosmetic composition of the invention, the benzene-1,4-[di(3-methylidene-10-camphosulphonic)] acid is present in proportions of between 0.1 and 10% by weight, and preferably between 0.5 and 5% by weight with respect to the total weight of the composition, before partial or total neutralization.

The photostable or photochemically stabilized UV-A filtering system in the oily phase represents between 0.1 and 15% by weight, and preferably between 0.5 and 10% by weight of the total weight of the composition.

In the case in which the photochemically stabilized compound 3 or compound 4 are used, a weight ratio of the stabilizing benzylidene camphor derivative(s) (compounds 5 to 8) to the dibenzoylmethane derivative(s) at least equal to 1 must be ensured.

For reasons of solubilization of the filters in the composition, this ratio is preferably less than or equal to 6.

The filtering cosmetic composition according to the invention can contain other filters, and in particular homomenthyl salicylate which is an oil-soluble UV-B filter, in proportions which can reach 6% by weight with respect to the total weight of the composition.

The filtering cosmetic composition according to the invention can be presented in the form of a cream or a milk, and can be packed in an aerosol. It has a pH of between 4 and 9, and preferably between 5.5 and 8. It can be adjusted using a normal alkalinizing or acidifying agent.

Glycerides such as mineral, animal or vegetable oils or waxes, fatty acids, fatty acid esters such as fatty acid triglycerides having from 6 to 12 carbon atoms, fatty alcohols, monoalcohols or lower polyols containing from 2 to 6 carbon atoms, or their mixtures can be used as solvent to dissolve the fat-soluble filters. The particularly preferred monoalcohols or polyols are ethanol, isopropanol, propylene glycol and glycerol.

The filtering cosmetic composition according to the invention intended to protect the human epidermis against ultraviolet rays can contain the normal cosmetic adjuvants for this type of composition, such as thickeners, emollients, humectants, emulsifiers, preservatives, antifoams, lanolin, fragrances, propellants, colourings and/or pigments having the function of colouring the composition itself or the skin, or any other ingredient which is normally used in cosmetics.

A subject of the invention is also a filtering cosmetic composition containing a high concentration of the filters defined above, this concentration being capable of reaching 50%, the filters being dissolved in a soap. This composition, or concentrate, is capable of being diluted in water or into an emulsion; a composition such as described above, which is intended to be applied to the skin, is thus obtained.

This concentrate contains from 10 to 17% of water-soluble filter (compound 1) and from 15 to 33% of oil-soluble filters (compounds 2 to 8), in a base constituted of a soap and water.

Preferably, a concentrate containing the following is used:
up to 17% of compound 1
up to 5.5% of compound 3
up to 27% of compound 6
12 to 15% of a fatty acid soap, the remainder being constituted of water.

The soap is generally triethanolamine stearate.

The following examples will illustrate the invention without, however, having a limiting character.

EXAMPLE 1

The following sunscreen emulsion is prepared:

| | |
|---|---|
| Compound 1 | 5 g |
| Compound 3 | 2 g |
| Compound 7 | 4 g |
| Compound 5 | 2 g |
| Mixture of cetylstearyl alcohol and cetylstearyl alcohol oxyethylenated with 33 moles of OE ("Sinnowax AO" sold by the Henkel company) | 7.5 g |
| Mixture of glycerol mono- and distearate ("Geleol copeaux" sold by the Gattefosse company) | 2 g |
| Cetyl alcohol | 1.8 g |
| Benzoate of $C_{12}$–$C_{15}$ fatty alcohols ("Finsolv TN" sold by the Finetex company) | 15 g |
| Propylene glycol | 5 g |
| Glycerol | 8 g |
| Triethanolamine | 3.4 g |
| Water qs | 100 g |

The fat-soluble filters 3, 7 and 5 are dissolved in the fatty phase which is heated to about 75°–80° C. The aqueous phase containing the glycerol, the emulsifier and the water-soluble filter 1 is heated to about 75°–80° C.; the fatty phase is added to the aqueous phase with brisk stirring. After 15 minutes of brisk stirring, the mixture is left to cool with moderate stirring.

EXAMPLE 2

The following sunscreen composition is prepared in the form of an emulsion:

| | |
|---|---|
| Compound 1 | 5 g |
| Compound 2 | 5 g |
| Mixture of cetylstearyl alcohol and cetylstearyl alcohol oxyethylenated with 33 moles of OE ("Sinnowax AO" sold by the Henkel company) | 7.5 g |
| Mixture of glycerol mono- and distearate ("Geleol copeaux" sold by the Gattefosse company) | 2 g |
| Cetyl alcohol | 1.8 g |
| Benzoate of $C_{12}$–$C_{15}$ fatty alcohols ("Finsolv TN" sold by the Finetex company) | 15 g |
| Propylene glycol | 5 g |
| Glycerol | 8 g |
| Triethanolamine | 3.4 g |
| Water qs | 100 g |

This emulsion is prepared in the same manner as in Example 1.

EXAMPLE 3

The following sunscreen composition is prepared in the form of an emulsion:

| | |
|---|---|
| Compound 1 | 5 g |
| Compound 3 | 1.5 g |
| Compound 8 | 5 g |
| Mixture of cetylstearyl alcohol and cetylstearyl alcohol oxyethylenated with 33 moles of OE ("Sinnowax AO" sold by the Henkel company) | 7.5 g |
| Mixture of glycerol mono- and distearate ("Geleol copeaux" sold by the Gattefosse company) | 2 g |
| Cetyl alcohol | 1.8 g |
| Benzoate of $C_{12}$–$C_{15}$ fatty alcohols ("Finsolv TN" sold by the Finetex company) | 15 g |
| Propylene glycol | 5 g |
| Glycerol | 8 g |
| Triethanolamine | 3.4 g |
| Water qs | 100 g |

This emulsion is prepared in the same manner as in Example 1.

EXAMPLE 4

The following filtering composition is prepared:

| | |
|---|---|
| Compound 1 | 3 g |
| Compound 3 | 3 g |
| Compound 6 | 3 g |
| Mixture of cetylstearyl alcohol and cetylstearyl alcohol oxyethylenated with 33 moles of OE ("Sinnowax AO" sold by the Henkel company) | 7 g |
| Mixture of non-autoemulsifiable glycerol mono- and distearate | 2 g |
| Benzoate of $C_{12}$–$C_{15}$ alcohols ("Finsolv TN" sold by the Finetex company) | 20 g |
| Cetyl alcohol | 1.5 g |
| Vasoline oil | 1.5 g |
| Polydimethylsiloxane | 1.5 g |
| Glycerol | 20 g |
| Triethanolamine | 1.8 g |
| Preservatives qs | |
| Water qs | 100 g |

This emulsion is prepared in the same manner as in Example 1.

EXAMPLE 5

The following sunscreen emulsion is prepared:

| | |
|---|---|
| Compound 1 | 3 g |
| Compound 3 | 1.5 g |
| Compound 6 | 4.5 g |
| Mixture of cetylstearyl alcohol and cetylstearyl alcohol oxyethylenated with 33 moles of OE ("Sinnowax AO" sold by the Henkel company) | 7 g |
| Mixture of non-autoemulsifiable glycerol mono- and distearate | 2 g |
| Benzoate of $C_{12}$–$C_{15}$ alcohols ("Finsolv TN" sold by the Finetex company) | 20 g |
| Cetyl alcohol | 1.5 g |
| Polydimethylsiloxane | 1.5 g |
| Glycerol | 20 g |
| Triethanolamine | 1.8 g |
| Preservatives qs | |
| Water qs | 100 g |

This emulsion is prepared in the same manner as in Example 1.

EXAMPLE 6

The following sunscreen emulsion is prepared:

| | |
|---|---|
| Compound 1 | 3 g |
| Parsol 1789 - compound 3 | 1 g |
| Compound 6 | 5 g |
| Homomenthyl salicylate | 4 g |
| Mixture of cetylstearyl alcohol and cetylstearyl alcohol oxyethoxylenated with 33 moles of OE ("Sinnowax AO" sold by the Henkel company) | 7 g |
| Mixture of non-autoemulsifiable glycerol mono- and distearate | 2 g |
| Triglycerides of capric and caprylic acids ("Miglyol 812" sold by the Dynamit Nobel company) | 30 g |
| Polydimethylsiloxane | 1.5 g |
| Cetyl alcohol | 1.5 g |
| Preservatives qs | |
| Water qs | 100 g |

This emulsion is prepared in the same manner as in Example 1.

EXAMPLE 7

The following concentrate is prepared:

| | |
|---|---|
| Compound 1 | 16.1 g |
| Compound 3 | 5.4 g |
| Compound 6 | 26.9 g |
| Stearic acid | 13.4 g |
| Triethanolamine | 10.7 g |
| Water qs | 100 g |

This concentrate is in the form of a paste which can be diluted to an emulsion or in water.

I claim:

1. A photostable filtering cosmetic concentrate composition for protecting the skin from UV radiation of wavelengths between 280 and 380 nm, consisting essentially of, in a base comprising a soap and water, an effective amount ranging from 10 to 17 weight percent of, as a wide absorption band photostable filter, benzene-1,4-[di(3-methylidene-10-camphosulphonic)] acid and an effective amount ranging from 15 to 33 weight percent of a photostable UV-A filtering system consisting essentially of an effective amount of at least one of (i) N-(2-ethylhexyl)-3-[(3'-methoxy-4'-n-butoxy)benzylidene]-10-camphosulphonamide, (ii) 4-(1,1-dimethylethyl)-4'-methoxydibenzoylmethane and (iii) 4-isopropyldibenzoylmethane, said (ii) and (iii) compounds being photochemically stabilized by at least one fat-soluble filter of $\lambda_{max}$ less than 330 nm selected from the group consisting of (iv) benzylidene camphor, (v) p-methylbenzylidene camphor, (vi) N-(2-ethylhexyl)-4-(3'-methylidene camphor) benzene sulphonamide and (vii) 3-methoxy-4-n-butoxybenzylidene camphor, the weight ratio of the at least one of said compound (iv), (v), (vi) and (vii) to said compound (ii) or compound (iii) being at least 1.

2. The photostable filtering cosmetic composition of claim 1 which contains

10–17 percent by weight of benzene-1,4-[di(3-methylidene-10-camphorsulphonic)] acid, up to 5.5 percent by weight of 4-(1,1-dimethylethyl)-4'-methoxydibenzoylmethane, up to 27 percent by weight of p-methylbenzylidene camphor, 12 to 15 percent by weight of a fatty acid soap, the remainder being water.

3. The photostable filtering cosmetic composition of claim 2 wherein the fatty acid soap is triethanolamine stearate.

* * * * *